(12) United States Patent
Sirota et al.

(10) Patent No.: US 8,236,168 B2
(45) Date of Patent: Aug. 7, 2012

(54) ONSET HAZE MEASUREMENT APPARATUS AND PROCEDURE

(75) Inventors: Eric B. Sirota, Flemington, NJ (US); James W. Gleeson, Burke, VA (US); Marykathryn Lee, Plainfield, NJ (US)

(73) Assignee: Exxonmobil Research and Engineering Company, Annandale, NJ (US)

( * ) Notice: Subject to any disclaimer, the term of this patent is extended or adjusted under 35 U.S.C. 154(b) by 332 days.

(21) Appl. No.: 12/587,710

(22) Filed: Oct. 13, 2009

(65) Prior Publication Data

US 2011/0083994 A1   Apr. 14, 2011

(51) Int. Cl.
C10G 61/04 (2006.01)
C10G 61/06 (2006.01)
C10G 73/02 (2006.01)
C10G 47/00 (2006.01)
G01N 25/12 (2006.01)

(52) U.S. Cl. .............. 208/62; 208/28; 208/58; 208/133; 374/20

(58) Field of Classification Search ............... 208/28, 208/58, 62, 133; 374/20
See application file for complete search history.

(56) References Cited

U.S. PATENT DOCUMENTS

| | | | |
|---|---|---|---|
| 2,038,420 A | 4/1936 | Coakley | |
| 2,038,604 A | 4/1936 | Robertson et al. | |
| 3,005,768 A * | 10/1961 | Burke | 208/28 |
| 3,202,826 A | 8/1965 | Greathouse | |
| 3,322,960 A * | 5/1967 | Geniesse | 250/576 |
| 4,474,672 A | 10/1984 | Herd et al. | |
| 4,519,717 A | 5/1985 | Jones et al. | |
| 4,541,719 A | 9/1985 | Wyatt | |
| 4,556,326 A | 12/1985 | Kitchen, III et al. | |
| 4,616,927 A | 10/1986 | Phillips et al. | |
| 4,628,204 A | 12/1986 | Maes | |
| 4,770,540 A | 9/1988 | Chague et al. | |
| 4,804,274 A | 2/1989 | Green | |
| 4,874,523 A | 10/1989 | LaFreniere | |
| 4,907,884 A | 3/1990 | Philips et al. | |
| 4,925,314 A | 5/1990 | Claudy et al. | |
| 5,007,733 A | 4/1991 | Laurent et al. | |
| 5,088,833 A | 2/1992 | Tsang et al. | |
| 5,572,320 A | 11/1996 | Reintjes et al. | |
| 5,641,230 A | 6/1997 | Okubo | |
| 5,651,614 A | 7/1997 | Juneau | |
| 5,661,233 A | 8/1997 | Spates et al. | |
| 5,708,196 A | 1/1998 | Tolvanen et al. | |
| 5,740,291 A | 4/1998 | De Lasa et al. | |
| 5,751,415 A | 5/1998 | Smith et al. | |
| 5,827,952 A | 10/1998 | Mansure et al. | |
| 5,831,721 A | 11/1998 | Alkafeef | |
| 5,905,271 A | 5/1999 | Wynn | |
| 6,028,667 A | 2/2000 | Smith et al. | |
| 6,035,706 A | 3/2000 | Campagnolo et al. | |
| 6,051,129 A | 4/2000 | Harris et al. | |
| 6,052,184 A | 4/2000 | Reed | |
| 6,076,959 A | 6/2000 | Nagasawa | |
| 6,456,375 B1 | 9/2002 | Ottens et al. | |
| 6,507,401 B1 | 1/2003 | Turner et al. | |
| 6,579,441 B1 | 6/2003 | Biscardi et al. | |
| 6,618,144 B1 | 9/2003 | Reed | |
| 6,651,009 B1 | 11/2003 | Trainoff et al. | |
| 6,653,150 B1 | 11/2003 | Reed | |
| 6,707,556 B2 | 3/2004 | Turner et al. | |
| 6,774,994 B1 | 8/2004 | Wyatt et al. | |
| 6,817,754 B2 | 11/2004 | Tsang et al. | |
| 6,827,484 B2 | 12/2004 | Tsang et al. | |
| 6,827,842 B2 | 12/2004 | Beasley et al. | |
| 6,839,137 B2 | 1/2005 | Mason et al. | |
| 6,841,779 B1 | 1/2005 | Roehner et al. | |
| 6,846,778 B2 | 1/2005 | Johnson et al. | |
| 6,881,760 B1 | 4/2005 | Smith et al. | |
| 6,962,651 B2 * | 11/2005 | Miller et al. | 208/95 |
| 6,966,692 B2 | 11/2005 | Tsang et al. | |
| 6,977,365 B1 | 12/2005 | Wynn | |
| 2004/0004717 A1 | 1/2004 | Reed | |
| 2005/0013740 A1 | 1/2005 | Mason et al. | |
| 2005/0112767 A1 | 5/2005 | Eagan et al. | |
| 2006/0098708 A1 | 5/2006 | Cleris et al. | |
| 2008/0250814 A1 * | 10/2008 | Marut et al. | 62/640 |

FOREIGN PATENT DOCUMENTS

| | | |
|---|---|---|
| DE | 2528912 A | 1/1977 |
| EP | 0 165 346 B1 | 4/1988 |
| EP | 0 102 726 B1 | 6/1988 |
| EP | 0 182 618 B1 | 7/1990 |
| EP | 0 171 300 B2 | 12/1992 |
| EP | 0 328 334 B1 | 11/1994 |
| EP | 0 723 155 A2 | 7/1996 |
| EP | 0712922 B1 | 2/2000 |
| EP | 0 851 220 B1 | 2/2005 |

(Continued)

OTHER PUBLICATIONS

Randy F. Alex, et al., "Determination of Cloud Point for Waxy Crudes Using a Near-Infrared/Fiber Optic Technique", *Energy & Fuels*, 1991, 5, pp. 866-868.

(Continued)

*Primary Examiner* — Randy Boyer

(74) *Attorney, Agent, or Firm* — Estelle Bakun; David Weisberg

(57) ABSTRACT

An apparatus and method for determining at least one of the temperatures at which a petroleum product will manifest delayed haze and the temperature at which haze will not exist in the product is provided. The apparatus comprises a container for holding a sample of the product, a light source, light detector, heaters and coolers combined with microprocessor means for storing and analyzing at least one of light transmitted or scattered by the sample. Measurements are useful in determining the haze properties of the product and also for controlling a dehazing process to meet target haze properties.

4 Claims, 4 Drawing Sheets

FOREIGN PATENT DOCUMENTS

| | | |
|---|---|---|
| EP | 1 507 136 A1 | 2/2005 |
| EP | 1 510 807 A1 | 3/2005 |
| EP | 0 792 449 B1 | 5/2005 |
| GB | 819121 | 8/1959 |
| GB | 1109731 | 4/1968 |
| GB | 2 360 830 B | 10/2001 |
| JP | 55106342 A2 | 8/1980 |
| JP | 6043959 B2 | 6/1994 |
| JP | 7244004 A | 9/1995 |
| SU | 1718055 A1 | 3/1992 |
| WO | WO 94/24544 | 3/1994 |
| WO | WO95/20153 | 7/1995 |
| WO | WO96/16325 | 5/1996 |
| WO | WO97/43612 | 11/1997 |
| WO | WO98/01748 | 1/1998 |
| WO | WO00/42398 | 7/2000 |
| WO | 00/77125 A1 | 12/2000 |
| WO | WO01/29534 A1 | 4/2001 |
| WO | WO01/40771 A2 | 6/2001 |
| WO | WO02/068941 A1 | 9/2002 |
| WO | WO2004/009733 A2 | 1/2004 |
| WO | WO2004/042385 A1 | 5/2004 |
| WO | WO2004/106916 A1 | 12/2004 |
| WO | WO2005/003754 A2 | 1/2005 |
| WO | WO2005/054843 A1 | 6/2005 |

OTHER PUBLICATIONS

Kenneth B. Bailey, et al., "Use of on-line petroleum test equipment for enhanced quality oversight and sampling of products transported by automated fungible piplne", Proceedings of the 7th International Conference on Stability and Handling of Liquid Fuels, Graz, Austria, Sep. 24-29, 2000, vol. 1, Edited by Harry N. Giles, Publisher: U.S. Department of Energy, Washington, DC.

Grzegorz Kozakowski, et al., "Method for Monitoring Effectiveness of Solvent Dewaxing of Lube Oils Base", Proceedings of the World Petroleum Congress, 1998, 15th, vol. 2, pp. 950-951.

Joao A. P. Coutinho, "The Limitations of the Cloud Point Measurement Techniques and the Influence of the Oil Composition on Its Detection", Petroleum Science and Technology, 23, 9-10, pp. 1113-1128, 2005.

Karl J. Siebert, "Haze formation in beverages", LWT—Food Science and Technology, 2006, 39, 9, pp. 987-994.

H. Tsuji, "Automatic Analyzer for Determination of Precipated Wax (Content) in Gas Oil", J. Japan Petroleum Institute, V29, No. 5, pp. 373-377 (Abstract Only).

Emanuele Vignati, "Wax crystallization and aggregation in a model crude oil", Journal of Physics: Condensed Matter, 2005, 17, 45, pp. S3651-S3660.

Nguyen X. Thanh, "Waxes and asphaltenes in crude oils", Organic Geochemistry, 1999, 30, 2/3, pp. 119-132.

P. Jokuty, et al., "A New Method for the Determination of Wax Content of Crude Oils", Environment Canada 20th Arctic and Marine Oil Spill Program (AMOP) Technical Seminar, Vancouver, Jun. 11-13, 1997, pp. 63-72.

B. Eisenberg, et al., "Exxon's Advanced Gas-to-Liquids Technology", 5th International Natural Gas Conversion Symposium, Giardini Naxos-Taormina, Italy, Sep. 20-25, 1998, Studies in Surface Science and Catalysis, V. 119, 1998, pp. 943-948.

"[A survey of] New Products [for gasoline manufacture]", Fuel Reformulation, vol. 5, No. 4, Jul.-Aug. 1995, pp. 54-55.

"New products/Automated cloud/pour point analyzer", Fuel Technology & Management, vol. 7, No. 5, Jun. 1997, pp. 62-63.

"Fuels testing, quality measurement and control", Hydrocarbon Asia, vol. 8, No. 6, Sep. 1998, pp. 60-62.

John F. Rabolt, et al., "Experimental Aspects of Fourier Transform Raman Spectroscopy", Mikrochimica Acta, 1988, 11, pp. 219-222.

Eiman M. Al-Muhareb, et al., "Size Exclusion Chromatography for the Unambiguous Detection of Aliphatics in Fractions from Petroleum Vacuum Residues, Coal Liquids, and Standard Materials, in the Presence of Aromatics", Energy & Fuels, 2006, 20, 3, pp. 1165-1174.

Jean Pierre Crine, et al., "Determination of Wax Content in Mineral Paraffinic Oils", Conference Record—Eighth International Conference on Conduction and Breakdown in Dielectric Liquids, Pavia, Italy, Jul. 24-27, 1984.

M. Al-Ahmad, et al., "Cloud Point Measurement of Base Oils", Erdoel Erdgas Kohle, vol. 113, No. 5, May 1997, pp. 219-220.

J. J. Spates, "Cloud Point Determination Using a Thickness Shear Mode Resonator", ACS 210th National Meeting, Chicago Aug. 20-25, 1995, ACS Division of Fuel Chemistry Preprints, vol. 40, No. 3, pp. 492-496.

E. F. Ghloum, et al., "Investigation of Asphaltene Precipitation Process for Kuwaiti Reservoir", Petroleum Science and Technology, 2004, 22, 7 and 8, pp. 1097-1117.

H. N. Frock, et al., "New Technology Gaining Acceptance in Oil Industry", Oilweek, Calcary, Alberta, vol. 32 No. 11, 38, Apr. 20, 1981.

"Product News: Testers Galore", Lubes-n-Greases, 8, 5, May 2002, p. 60.

N. Pasadakis, et al., "Prediction of the distillation profiles and cold properties of diesel fuels using mid-IR spectroscopy and neural networks", Fuel, 2006, 85, 7-8, pp. 1131-1137.

M. P. Esel Son, et al., "The Analyzer AMP-2 for Determination of Oil Present in Paraffin Wax", Khim I Tekhnol Topliv 1 Masel, vol. 10, No. 5, May 1965, pp. 40-42.

S. Seta, "Specifications/Fuels testing, quality measurement and control", Petroleum Review, vol. 52, No. 618, Jul. 1998, pp. 42-43.

"News/Technology: On-line petroleum analyzer offers continuous checks", Petroleum Review, vol. 53, No. 625, Feb. 1999, p. 49.

"Multi-function analyzer for ASTM tests", Petroleum Review, vol. 53, No. 624, Jan. 1999, pp. 39.

F. Davidson, et al., "An effective self-cleaning membrane filter and its applications to a new genersation of freeze and cloud point analyzers", Hydrocarbon Processing, vol. 76, No. 1, Jan. 1997, pp. 95-96, 98.

Charles Tsang, et al., "An effective self-cleaning membrane filter and its applications to a new generation of freez and cloud point analyzers", Proceedings of the Annual ISA Analysis Division Symposium, 1997, 30, pp. 155-166.

Gordon Chiu, "Innovative self-contained and small online analyzers for freeze, cloud, and pour point", Technical Papers of ISA, 2003, 444, pp. 230-238.

I. K. Yudin, et al., "Universal behavior of asphaltene aggregation in hydrocarbon solutions", Petroleum Science and Technology, 1998, 16, 3&4, pp. 395-414.

I. K. Yudin, et al., "Crossover from reaction-limited aggregation to diffusion-limied aggregation of asphaltenes in hydrocarbon solutions", Porous Media : Physics, Models, Simulation, Proceedings of the international Conference, Moscow, Nov. 19-21, 1997, pp. 75-84.

B. J. A. Bjoerkvik, et al., "Description of an interface light-scattering spectromete with a cylindrical high-pressure scattering cell including performance test on a model gas-condensate system", Journal of Colloid and Interface Science, 1994, 164, 1, pp. 151-162.

* cited by examiner

ONSET HAZE MEASUREMENT APPARATUS AND PROCEDURE

FIELD OF THE INVENTION

The present invention relates to a method and apparatus for measuring haze in liquids. In particular, this invention relates to a method and an apparatus to test for delayed onset haze or haze disappearance temperature in liquids by use of light scattering measurements and a procedure for using the apparatus.

The apparatus and method described herein are suitable for use with any material capable of transmitting light. However, the invention is particularly applicable for monitoring delayed onset haze or haze disappearance temperature in petroleum products such as heavy lubricant base stocks and especially in base stocks derived from gas-to-liquid (GTL) materials. Therefore, for convenience, the invention will be described by specific reference to petroleum products and especially lubricant base stocks and GTL derived base stocks.

BACKGROUND OF THE INVENTION

Petroleum products, such as fuels and lubricants, are characterized in part by the physical changes they exhibit at certain temperatures. Indeed, these temperature related changes are commonly used as specifications for fuels and lubricants. One such change is the hydrocarbon's cloud point. As is well known, the cloud point is the temperature at which dissolved solids in a fuel or lubricant, such as paraffin wax, begins to form and separate from the hydrocarbon. Another important property of fuels and lubricants is their pour point. The pour point is the lowest temperature at which the petroleum product will flow. Both cloud point and pour point are properties that can be critical to the performance of the fuel or lubricant.

Standard tests have been developed by the American Society for Testing Materials (ASTM) to determine cloud and pour point temperatures such as ASTM D2300-91 and ASTM D97-87. Both these tests require hands-on manipulation of petroleum product samples to determine the cloud and pour point temperatures.

Somewhat more sophisticated devices have been developed for measuring the cloud point of a petroleum product which are largely based on some optical measurement of an appropriately cooled sample.

Another physical property of petroleum products, which is important at least from an aesthetic and economic aspect, is their appearance. Products that are clear and bright are more highly valued than those that are hazy. Thus, in preparing a petroleum product such as a finished heavy lubricant base stock, a dewaxed oil will be subjected to a dehazing step to improve its appearance. As is known, dehazing is typically achieved by either catalytic or absorptive methods or by filtration to remove those constituents that result in haziness. Experience has shown, however, that a lubricant base stock may be produced that has a satisfactory cloud and pour point and that is clear and bright right after it is cooled to room temperature but may upon storage develop a haze. This phenomenon is referred to herein as delayed onset haze formation. Because delayed onset haze often does not manifest itself for an extended period of time, often as long as six months, it is difficult to know whether the lubricant will develop a haze during its expected shelf life. The temperature at which haze will not exist in the petroleum product is referred to herein as the haze disappearance temperature. Clearly it is highly desirable to be able to monitor and control the lubricant forming process to assure that the finished lubricant base stock has an acceptable delayed onset haze property or haze disappearance temperature.

While light scattering techniques have been used to measure various lubricant properties such as cloud and pour point, the use of such techniques to monitor and control delayed onset haze formation or haze disappearance temperature has not heretofore been explored or achieved.

Therefore, a need exists for an apparatus and method for rapidly determining whether a petroleum product will manifest delayed onset haze formation and the temperature at which haze will not exist. A need also exists for an apparatus which can be utilized on line and in real time with a petroleum process to control the process to produce products having predetermined haze properties.

The present invention is directed toward meeting the foregoing needs as well as other needs as embodied and broadly described herein.

SUMMARY OF THE INVENTION

In one embodiment of the invention there is provided a method for determining the temperature at which a petroleum product will manifest delayed onset haze and conversely the minimal temperature at which haze will not exist in the petroleum product (referred to as the haze disappearance temperature).

The method comprises irradiating a sample of the product with light while cooling the sample to below room temperature, to target temperature at about or below the cloud point of the sample. Light transmitted through the sample is measured and used to determine the delayed haze onset temperature. Thereafter, the sample is heated to an elevated temperature, typically in the range of about 60° C. to 80° C. at a preselected controlled rate, and the light transmitted through the sample is measured and used to determine the haze disappearance temperature.

In another embodiment of the invention, the method is used to monitor a product being produced and to control process variables, especially dewaxing and dehazing process variables, to provide a product having a preselected haze disappearance temperature.

These and other embodiments of the invention are achieved with an apparatus comprising a container for holding a sample having an optical pathway therethrough. The apparatus includes means for projecting a beam of light along the optical pathway and means for detecting light exiting the optical pathway. Means also are provided for cooling and heating the sample at a controlled, preselected rate while simultaneously detecting the light transmitted through the sample.

BRIEF DESCRIPTION OF THE DRAWINGS

In FIGS. 3 to 4, OPBU used therein refers to the Optical Phase Behavior Unit of the invention.

DETAILED DESCRIPTION OF THE INVENTION

Figure 1:
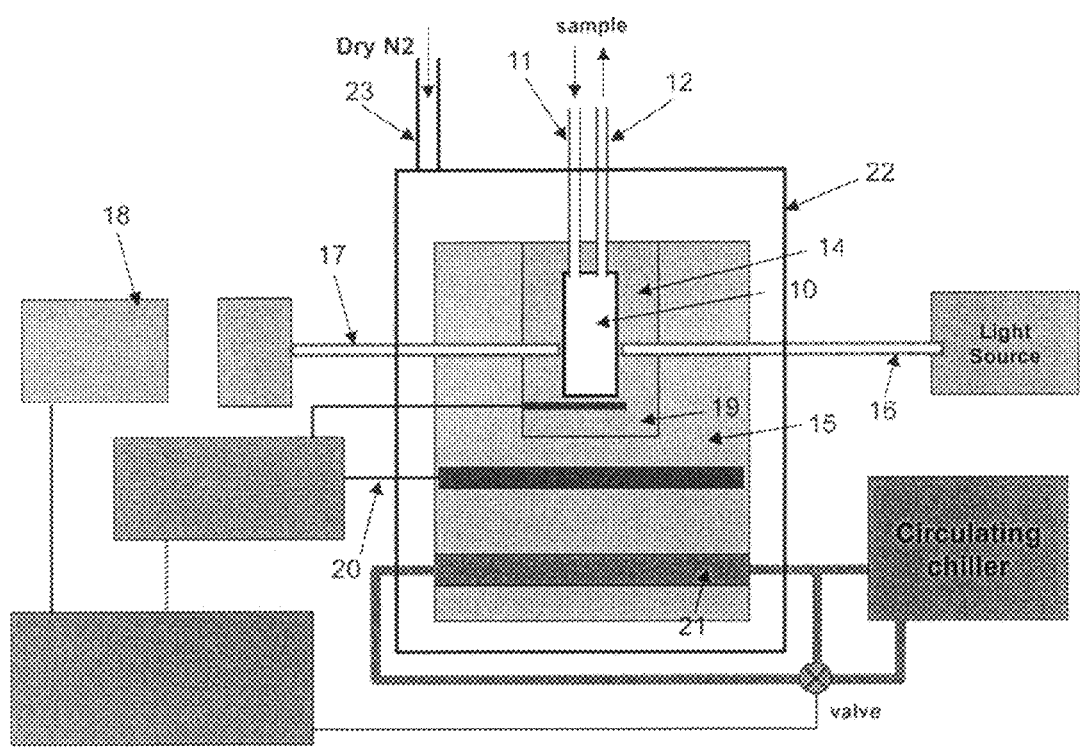
FIG. 1 is a schematic illustration of one embodiment of the apparatus of the invention.

The present invention is directed to a method and an apparatus for monitoring at least one of the delayed haze onset property and the haze disappearance temperature of liquid petroleum products, such as heavy lubricating oils. The invention is especially useful for liquid petroleum products that when produced are clear and bright but develop haze upon standing. According to the present invention, the delayed haze onset property or its haze disappearance temperature can be determined by an optical monitoring system that is operably coupled to a dewaxing or dehazing process controller or both, that permits immediate control of process variables to assure the production of a product meeting appropriate haze properties.

The petroleum products that may be advantageously monitored by the method of the invention especially include heavy lubricant base stock compositions comprising natural or synthetic dewaxed oils having low temperature properties able to meet target specifications or requirements and that are clear and bright when produced.

In one embodiment of the invention, the base stock is a gas-to-liquid (GTL) base stock and preferably a heavy lubricating oil GTL base stock. By heavy lubricating oil GTL base stock is understood to be one having a kinematic viscosity at 100° C. greater than about 8 cSt, preferably greater than about 10 cSt and more preferably greater than about 12 cSt. As is known in the art, GTL base stocks are materials of lubricating viscosity that are generally derived from waxy synthesized hydrocarbons that are themselves derived from simpler gaseous carbon-containing compounds, hydrogen-containing compounds and/or elements as feedstocks. The preferred GTL material from which the GTL base stock is derived is the high alpha waxy hydrocarbons produced in a Fischer-Tropsch synthesis process. By high alpha is meant an alpha of at least 0.85, preferably at least 0.9 and more preferably at least 0.92. As used herein, alpha refers to the Schultz-Flory kinetic alpha.

In general, the waxy feed from which the natural or synthetic oil is produced will have an initial boiling point in the range of 650-750° F. and preferably continuously boils up to an end point of at least 1050° F.

The process for making lubricant base stocks from waxy feeds may be characterized as an isomerization process. Typically, the process is conducted in the presence of at least one catalyst at temperatures in the range of from about 150° C. to about 500° C. at pressures ranging from about 500 to 20,000 kPa. The process may be operated in the presence of hydrogen and hydrogen partial pressures ranging from about 600 to 6,000 kPa. The ratio of hydrogen to hydrocarbon feedstock typically ranges from about 10 to 3,500 n.l.l.$^{-1}$ (56 to 19,660 SCF/bbl), and the space velocity of the feedstock typically ranges from about 0.1 to 20 LHSV.

The dewaxing step may be accomplished using one or more of solvent dewaxing, catalytic dewaxing or hydrodewaxing.

In solvent dewaxing, the isomerized wax product is contacted with chilled solvents such as acetone, methylethyl ketone (MEK), methylisobutyl ketone (MIBK), mixtures of MEK/MIBK and the like to precipitate the higher pour point material as a waxy solid which is then separated from the solvent-containing lube oil fraction. The solvent is then stripped out and dewaxed oil may be fractioned and, if necessary, be subjected to dehazing.

Catalytic dewaxing typically employs shape selective molecular sieves that are combined with at least one catalytic metal component. Typical catalytic dewaxing conditions include a temperature in the range of from about 400-600° F., a pressure of 500-900 psig, $H_2$ treat rate of 1500-3,500 SCT/B for flow through reactors and LHSV of 0.1-10.

The dewaxed base stock optionally and preferably is subjected to mild dehazing to improve its color, appearance and stability.

Dehazing typically is achieved by either catalytic or absorptive methods, well known in the, to remove those constituents that result in haziness.

One embodiment of an apparatus useful in the method of the invention will be discussed with reference to FIG. 1.

As shown in FIG. 1, a cuvette 10 is provided for holding the sample to be tested. Cuvette 10 may be open on top with a cap (not shown) and filled manually or provided with inlet and outlet conduits 11 and 12 respectively for use in a flow through mode. Cuvette 10 has optical windows on opposite sides. Cuvettes are currently available with spacings between the windows for standard path lengths of 0.5 mm, 1 mm, 2 mm, 5 mm and 10 mm. In the practice of the invention, it is preferred to use a cuvette with a path length of 10 mm. The cuvette 10 is contained within a cuvette holder 14 within a metal block 15, preferably of aluminum. Fiber optic cable 16 is provided for emitting light from an associated light source into a sample contained in cuvette 10. Preferably, the light source emits visible light. A fiber optic cable 17 is longitudinally aligned with cable 16 for receiving light transmitted through the sample in cuvette 10. Optical cable 17 is electronically connected to programmable logic controller 18, which electronically records and stores the amount of light detected by cable 17. Heating means 20 is positioned within metal block 15 and is in operable communication with programmable logic controller 18. Metal block 15 also includes a fluid channel 21 for circulating a chilled fluid for cooling block 15. Circulation of chilled fluid is controlled by the programmable logic controller 18. A temperature sensor 19 is positioned within cuvette holder 14 in sufficiently close proximity to the cuvette 10 to detect the temperature of a sample in the cuvette. Temperature sensor 19 also is in operable communication with logic controller 18. Because the sample in cuvette 10 will be cooled below room temperature, block 15 is positioned within an enclosure 11 through which dry nitrogen may be circulated via conduit 23. This enclosure provides for the ability to keep the dew point around the block 15 below the lowest temperature of interest.

The principle upon which the apparatus is based resides in the fact that lubes are substantially transparent in the absence of haze. Thus, light will pass through a lube without absorption or scattering resulting in a transmission of essentially unity. Haze platelets formed in a lubricant by crystallizing paraffins scatter light. Thus, the amount of light transmitted by a haze lubricant will decrease due to light scattering. Because haze formation is a nucleation dominated process, the scattered intensity and the decrease in transmitted intensity will be proportional to the concentration of haze as well as the path length through the lubricant. Thus, if a 0.1 mm path length with a given haziness decreases the transmitted intensity to 0.99 of the initial intensity, then a 1 mm path length will give 0.9910=0.904, and a 10 mm path length will decrease the intensity to 0.99100=0.37. Using transmission geometry, the sensitivity of the instrument can be increased by changing the path length of the cell.

To determine the delayed onset haze formation temperature of a dewaxed clear and bright lubricant basestock, a sample of the basestock is placed in cuvette 10 within cuvette holder 14. This can be achieved by manually placing a sample in the cuvette 10 or by flowing a stream, e.g., a slip stream from the dewaxing or dehazing process, into the cuvette 10. When the sample is placed in the cuvette, it is important that it had been maintained under conditions sufficient to prevent any nucleation of haze-forming constituents. Thus, the sample at the time of placement in the cuvette should have been at an elevated temperature in the range of about 80° C. to 120° C. for about 10 to 30 minutes. Optionally, but preferably, after placing the sample in cuvette 10, the sample is heated by heater 20 to about 90° C. for about 20 minutes to assure denucleation of any haze-forming constituents. The denucleation of haze-forming constituents may be determined by any convenient means, such as, measuring the light transmission through the sample. The temperature of the sample is then decreased to about 40° C. over about 10 minutes by circulation of chilled fluid through conduit 21 prior to the data-taking cooling ramp.

The sample also may be, and preferably is, subjected to conditions sufficient to ensure homogeneity of the sample. Such conditions can include shaking or stirring in the cuvette 10. Alternatively, the sample can be heated and agitated in a separate container and then transferred to the cuvette 10.

Next, the sample is cooled below room temperature to a target temperature at about or below the cloud point temperature of the sample. In general, the target temperature will be about −10° C. The cooling is conducted at a constant rate generally in the range of about 1 to 0.1 degrees/minute and preferably at a 0.5 degrees/minute.

While the sample is being cooled to the target temperature, light is continuously emitted into the sample by fiber optic cable 16, and the transmitted light is received by fiber optic cable 17 and is processed by programmable logic controller 18.

Among other functions, the controller 18 is programmed to convert the raw data of transmitted intensity versus time (I raw (t)) to intensity versus temperature (I raw (T)) The intensity is then normalized to the intensity at the beginning of the run when no haze is present ($I(T)=I\ raw\ (T)/I_o$). The difference between this and unity is a measure of the scattered intensity and the amount of haze ($H(T)=1-I(T)$). As the temperature of the sample is reduced, $H(T)$ will increase from zero to a threshold value, $H_t$. The temperature where $H(T)=H_t$ is $T_{haze}$.

To determine the maximum temperature at which haze may appear in the sample, the temperature ramp is reversed, and the sample is heated preferably at a fixed rate which optionally may be the same rate as the cooling rate while the light transmitted through the sample is monitored. The point at which $H(T)$ decreases to the baseline or an extrapolation of the fastest falling portion of $H(T)$ to the baseline is considered to be the haze disappearance temperature. The haze disappearance temperature represents the equilibrium disappearance temperature for the haze and is the temperature above which haze will never form.

Figure 2:
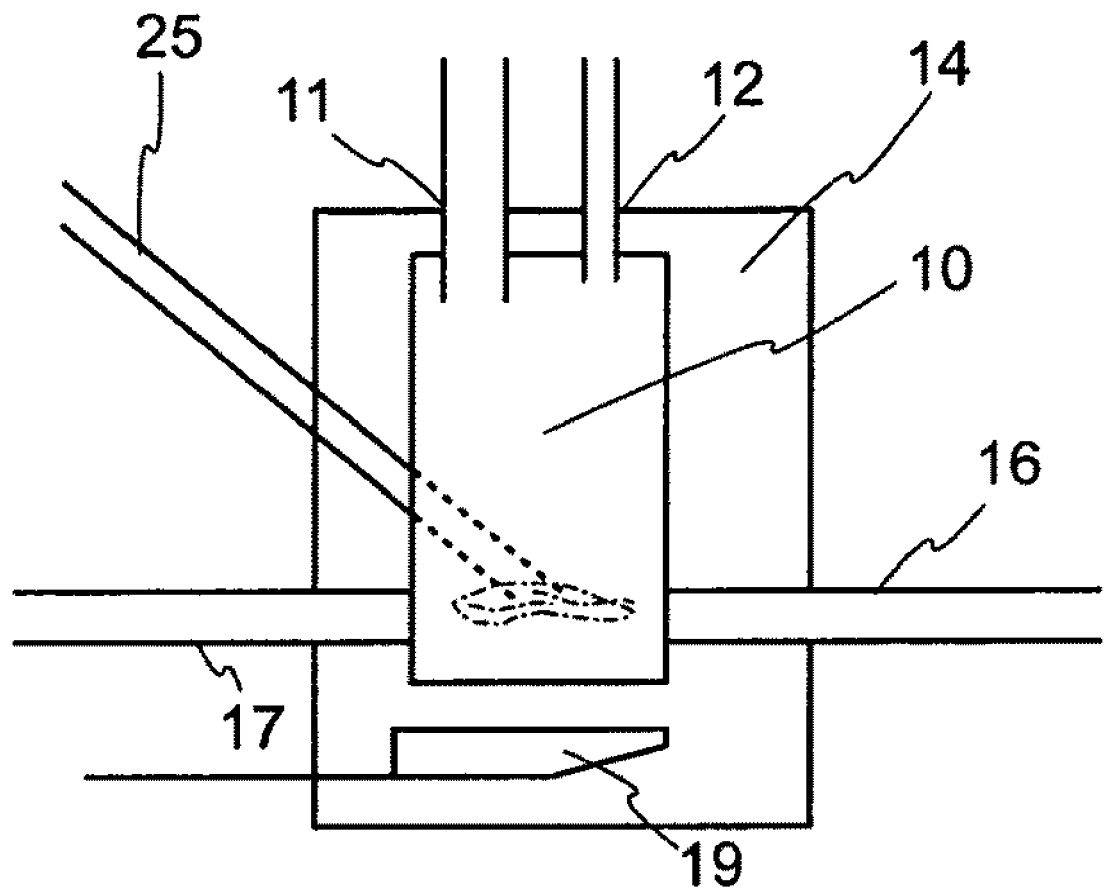
FIG. 2 is a schematic illustration of an alternate embodiment of the invention in which means are provided for capturing scattered light for detection and analysis.

Reference now is made to FIG. 2, which illustrates a preferred embodiment of the invention. This embodiment differs from that of FIG. 1 in that means are provided to detect and measure light scattered by a sample. As shown in FIG. 2, a fiber optic cable 25 is positioned at an angle with respect to the optical window in cuvette 10 that is opposite fiber optic cable 16. In the FIG. 2 embodiment, optical cable 25 is shown at a 45 degree angle, but other finite angles may be used. The selection of the angle will depend upon the desired sensitivity of the instrument with smaller angles believed to be more sensitive. In this embodiment, during the cooling and heating of the sample in cuvette 10, the light scattered by the sample is stored and analyzed. Fiber optic cable 25 may be operably connected to a photomultiplier tube (not shown) or similar device for use in detecting and measuring the amount of scattered light detected by the programmable logic controller. Optionally, the apparatus of this embodiment may also include fiber optic cable 17 for measuring transmitted light as well which can be used for calibration and consistency checks.

In one embodiment of the invention, the dewaxing or the dehazing of a lubricant basestock to provide a finished basestock can be monitored in accordance with the invention to determine the haze disappearance temperature of the finished basestock, and the dewaxing or dehazing process conditions can be controlled in real time to provide a finished basestock having a predetermined haze disappearance temperature.

Figure 3:
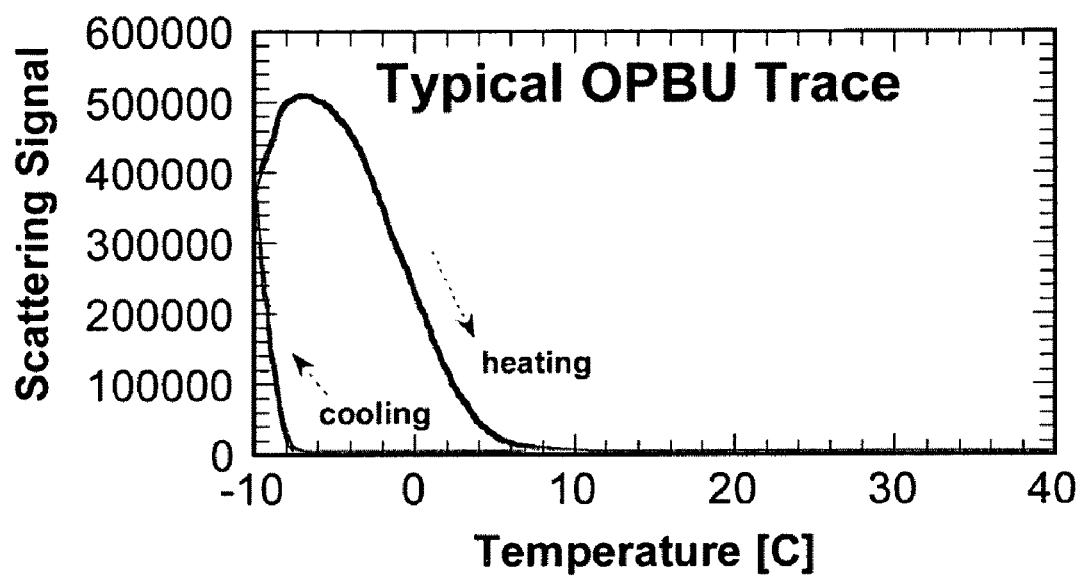
FIGS. 3 and 4 are plots that illustrate the optical behavior of a lubricating basestock analyzed according to the method of the invention.

Referring now to FIG. 3, a graphical plot of the results obtained with a device of FIG. 2 on a dewaxed GTL basestock is provided. The basestock used was clear and bright and had a VI of 150, a Kv at 40° C. of 139 and a Kv at 100° C. of 18.5. The test began with the sample at 40° C. The sample was cooled at a rate of 0.5° C./min. Upon cooling, the light scattering began at about −8° C. and continued with further cooling. Upon heating, the amount of light scattered decreases until the haze disappearance temperature is reached.

Figure 4:
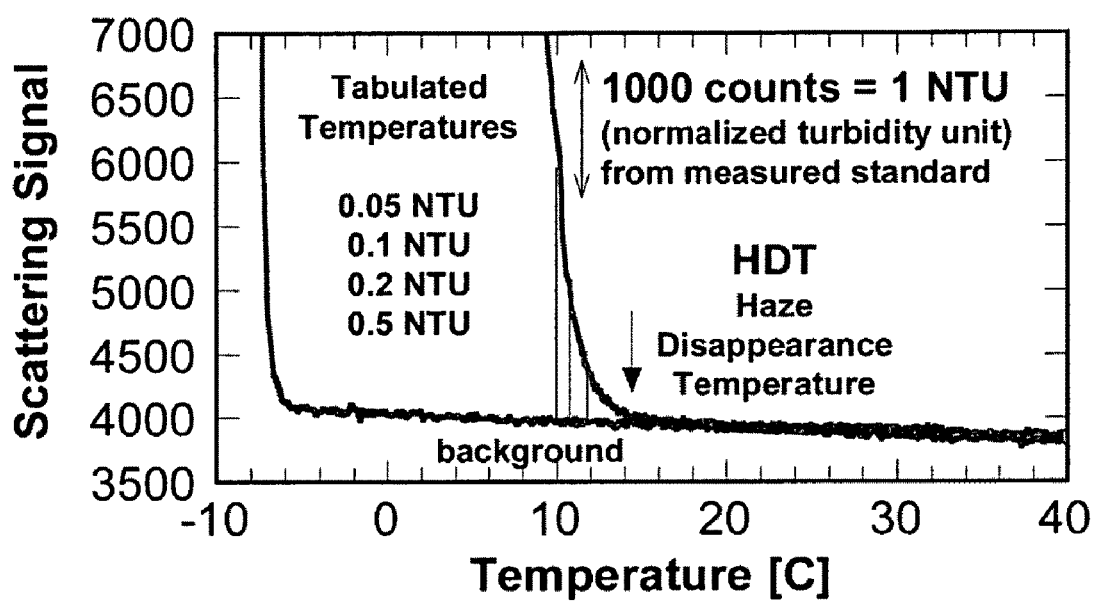

FIG. 4 is an expanded scale of FIG. 3 in which HDT is read by the return to the base line. The NTUs shown in FIG. 4 are calibrated by putting into the cuvette an NTU turbidity standard of 8 NTUs and measuring the light scattering. Thus, the scattering counts can be related to an industry acknowledged standardized turbidity unit.

It is apparent from the foregoing that the invention has a number of important features and advantages. It permits the measurement of the onset and disappearance of subtle haze. These measurements can be made rapidly. Indeed, the measurements can be made in real time to monitor the quality of a petroleum product being produced and to control process variables to meet product specifications.

While different embodiments of the invention have been described in detail herein, it will be appreciated by those skilled in the art that various modifications and alternatives to the embodiments could be developed that are within the breadth and scope of the invention illustrated and claimed herein.

What is claimed is:

1. A method for producing a heavy lubricant base stock from a high alpha GTL waxy hydrocarbon wherein the base stock has a preselected haze disappearance temperature, the method comprising:
   isomerizing the GTL waxy hydrocarbon under isomerization conditions to form an isomerized feed;
   dewaxing the isomerized feed to a preselected cloud and pour point to provide a dewaxed feed;
   subjecting the dewaxed feed to a dehazing step including cooling and filtering to provide a dehazed feed;
   measuring the haze disappearance temperature of the dehazed feed and when necessary adjusting the dehazing conditions to provide a dehazed feed having the preselected haze disappearance temperature, wherein the haze disappearance temperature is measured by
   (a) heating a sample of the basestock to about 90° C. for about 20 minutes;
   (b) cooling the so heated sample to about 40° C. over about 10 minutes;
   (c) then further cooling the sample at a rate of about 0.5 degrees/minute to about −10° C.;
   (d) followed by heating the sample at a constant rate; while simultaneously
   (e) projecting a beam of light along an optical pathway in the sample;
   (f) detecting the light scattered at an 45° angle to the optical pathway by means of a photomultiplier;

(g) measuring the temperature of the sample during cooling and heating; and (h) analyzing the light detected to determine the haze disappearance temperature.

2. In the method of producing a finished lubricating basestock by dewaxing an isomerized waxy hydrocarbon to a preselected cloud and pour point and dehazing the dewaxed hydrocarbon to provide a finished basestock, the improvement comprising measuring the haze disappearance temperature of the basestock as it is produced and when necessary adjusting the dehazing conditions to provide a basestock having a predetermined haze disappearance temperature, wherein the measuring of the haze disappearance temperature comprises (a) heating a sample of the basestock to about 90° C. for about 20 minutes;

(b) cooling the so heated sample to about 40° C. over about 10 minutes;

(c) then further cooling the sample at a rate of about 0.5 degrees/minute to about −10° C.;

(d) followed by heating the sample at a constant rate; while simultaneously (e) projecting a beam of light along an optical pathway in the sample;

(f) detecting the light scattered at an 45° angle to the optical pathway by means of a photomultiplier;

(g) measuring the temperature of the sample during cooling and heating; and (h) analyzing the light detected to determine the haze disappearance temperature.

3. The improvement of claim 2 wherein the haze disappearance temperature is measured in real time.

4. The improvement of claim 3 wherein the haze disappearance temperature is measured on a slip stream of the base stock.

* * * * *